US00PP08549P

United States Patent [19]

VandenBerg

[11] Patent Number: Plant 8,549

[45] Date of Patent: Jan. 18, 1994

[54] CHRYSANTHEMUM PLANT NAMED CHERRY PAPILLON

[75] Inventor: Cornelis P. VandenBerg, Salinas, Calif.

[73] Assignee: Yoder Brothers, Inc., Barberton, Ohio

[21] Appl. No.: 826,068

[22] Filed: Jan. 27, 1992

[51] Int. Cl.[5] ..... A01H 5/00

[52] U.S. Cl. ..... Plt./82.4

[58] Field of Search ..... Plt. 82.4, 82.5, 74.1

[56] References Cited

U.S. PATENT DOCUMENTS

Plt. 7,435 1/1991 Vanen Berg .....PLT/82.5
4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:526-530.

Gosling, ed., 1979, "The Chrysanthemum Manual—6th edition", The National Chrysanthemum Society, London, Essex Telegraph Press, Ltd., pp. 329-336.

Broertjes, et al., 1978, "Application of Mutation Breeding Methods in the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of chrysanthemums", Euphytica, 15:156-162.

Dowrick et al., 1966, "The induction of mutations in Chrysanthemum using X- and gamma radiation", Euphytica, 15:204-210.

*Primary Examiner*—Howard J. Locker
*Attorney, Agent, or Firm*—Foley & Lardner

[57] ABSTRACT

A Chrysanthemum plant named Cherry Papillon particularly characterized by its flat capitulum form; daisy capitulum type; greyed-red ray floret color; diameter across face of capitulum of 35 to 37 mm when fully opened, when grown as a pinched spray pot mum; photoperiodic flowering response to short days of 47 to 57 days; plant height, with 14 to 15 long days after sticking unrooted cuttings, and with 0 to 2 applications of 2500 ppm B-9 SP, ranges from 20 to 25 cm when grown as a pinched pot mum with 4 cuttings in a 15 cm pot; small dark green foliage; branching pattern is spreading and very prolific, each plant having 6 to 8 laterals after pinch; and very floriferous, with an excellent display of many small flowers.

1 Drawing Sheet

The present invention relates to a new and distinct cultivar of Chrysanthemum, botanically known as *Dendranthema grandiflora*, and referred to by the cultivar name Cherry Papillon.

Cherry Papillon, identified as 4165 (86-720A02), is a product of a mutation induction program. The new cultivar was discovered and selected by Cornelius P. VandenBerg on Mar. 20, 1990 in a controlled environment in Salinas, Calif., as one flowering plant within a flowering block established as rooted cuttings from stock plants which had been exposed as unrooted cuttings to an X-ray source of 2000 rads in Fort Myers, Fla., on Aug. 10, 1989. The irradiated parent cultivar was the cultivar identified as Papillon, disclosed in U.S. Plant Pat. No. 7,435, and described as a daisy spray pot mum with a flat capitulum form; a red-purple ray floret color; diameter across face of capitulum of 35 to 37 mm when fully opened; flowering response period of 47 to 57 days after start of short days; plant height of 18 to 28 cm with 1 to 2 applications of 2500 ppm B-9 SP when grown as a pinched pot mum in a 15 cm pot; small dark green foliage; spreading and very prolific branching pattern, with 6 to 8 laterals after pinch; and very floriferous, with an excellent display of many small flowers.

The irradiation program resulting in Cherry Papillon had as its primary objective the expansion of color ranges of the parent cultivar Papillon. The irradiation program comprised irradiating cuttings of the parent cultivar at irradiation levels of 1500, 1750 and 2000 rads. A total of 1554 cuttings harvested from a total of 225 irradiated plants were planted on Jan. 1, 1990, Dec. 11, 1989 and Nov. 27, 1989. Of these, 8 initial selections were made, which selections were then revegetated and reflowered. Three consecutive flowerings resulted in discarding 7 of the 8 selections on Dec. 7, 1990. The one remaining selection will be introduced as Cherry Papillon.

The first act of asexual reproduction of Cherry Papillon was accomplished when vegetative cuttings were taken from the initial selection in May 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Cherry Papillon are firmly fixed and are retained through successive generations of asexual reproduction.

Cherry Papillon has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Cherry Papillon, which, in combination, distinguish this Chrysanthemum as a new and distinct cultivar:

1. Flat capitulum form.
2. Daisy capitulum type.
3. Greyed-red ray floret color.
4. Diameter across face of capitulum of 35 to 37 mm when fully opened, when grown as a pinched spray pot mum.
5. Photoperiodic flowering response to short days of 47 to 57 days.
6. Plant height, with 14 to 15 long days after sticking unrooted cuttings, and with 0 to 2 applications of 2500 ppm B-9 SP, ranges from 20 to 25 cm when grown as a pinched pot mum with 4 cuttings in a 15 cm pot.
7. Small dark green foliage.
8. Branching pattern is spreading and very proliferic, each plant having 6 to 8 laterals after pinch.
9. Very floriferous, with an excellent display of many small flowers.

The accompanying photographic drawing is a side view of a potted mum of Cherry Papillon, with 4 cuttings in a 15 cm pot, with the colors being as nearly true as possible with illustrations of this type.

Of the commercial cultivars known to the inventor, the most similar in comparison to Cherry Papillon is the parent cultivar Papillon. All traits of Cherry Papillon are similar to those of Papillon, except for the ray floret color and the color retention. The ray floret color of Cherry Papillon is described as greyed-red, while the ray floret color of Papillon is red-purple. The color of Cherry Papillon fades relatively fast to a lighter bronze (about RHS 179C), with the ray florets of Papillon fading considerably less.

In the following description color references are made to the Royal Horticultural Society Colour Chart. The color values were determined on plant material grown as a pinched spray pot mum in Salinas, Calif. on Dec. 12, 1990.

Classification:

*Botanical.*—*Dendranthema grandiflora* cv Cherry Papillon.

*Commercial.*—Flat daisy spray pot mum.

INFLORESCENCE

A. Capitulum:
- *Form.*—Flat.
- *Type.*—Daisy.
- *Diameter across face.*—35 to 37 mm when fully opened.

B. Corolla of ray florets:
- *Color (general tonality from a distance of three meters).*—Greyed-red.
- *Color (upper surface).*—Closest to 180C.
- *Color (under surface).*—Closest to 181D.
- *Shape.*—Straight, oblong, slightly ribbed.

C. Corolla of disc florets:
- *Color (mature).*—Closest to 12A.
- *Color (immature).*—Closest to 3A.

D. Reproductive organs:
- *Androecium.*—Present on disc florets only; moderate pollen.
- *Gynoecium.*—Present on both ray and disc florets.

PLANT

A. General appearance:
- *Height.*—20 to 25 cm when grown as a pinched pot mum with 14 to 15 long days after sticking unrooted cuttings, and with 0 to 2 applications of 2500 ppm B-9 SP.
- *Branching pattern.*—Spreading and very prolific, each plant having 6 to 8 laterals after pinch.

B. Foliage:
- *Color (upper surface).*—147A.
- *Color (under surface).*—147B.
- *Shape.*—Small, lobed and slightly serrated.

I claim:

1. A new and distinct Chrysanthemum plant named Cherry Pappilon, as described and illustrated.

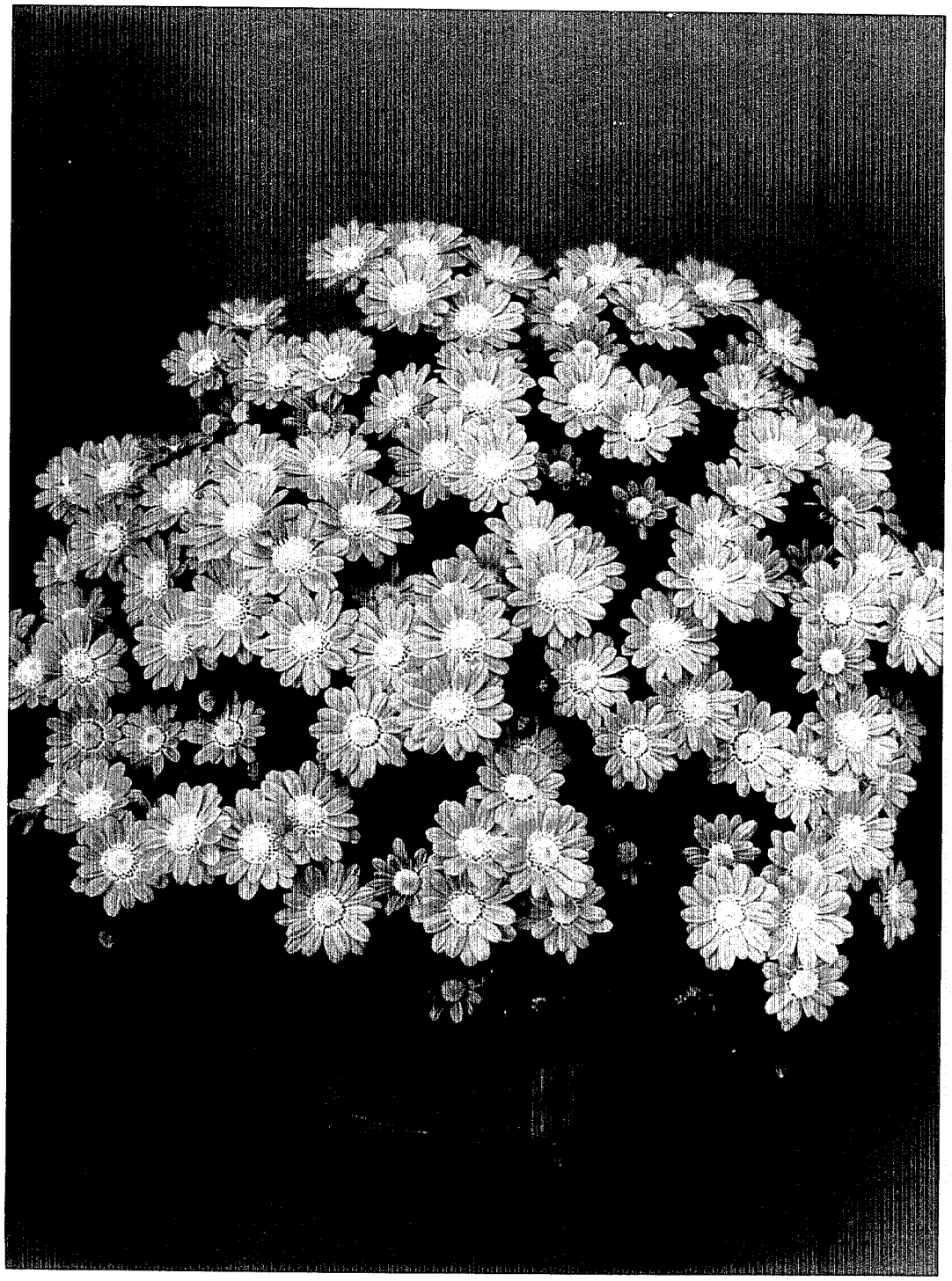

* * * * *